United States Patent [19]

Saito et al.

[11] 4,230,636

[45] Oct. 28, 1980

[54] PROCESS FOR PRODUCING DIMETHYL FORMAMIDE

[75] Inventors: Masao Saito; Tetsuo Aoyama; Shigeru Horie; Kazuo Takada, all of Niigata, Japan

[73] Assignee: Mitsubishi Gas Chemical Company, Inc., Tokyo, Japan

[21] Appl. No.: 917,894

[22] Filed: Jun. 22, 1978

[30] Foreign Application Priority Data

Jun. 24, 1977 [JP] Japan .................................. 52-75246

[51] Int. Cl.$^3$ ............................................ C07C 103/36
[52] U.S. Cl. .................................. 260/561 R; 252/443
[58] Field of Search ...................... 260/561 R; 252/443

[56] References Cited

U.S. PATENT DOCUMENTS

| 2,677,706 | 5/1954 | Giachino | 260/561 R |
| 2,793,211 | 5/1957 | Cicero | 260/561 R X |
| 2,866,822 | 12/1958 | Siefen et al. | 260/561 R |
| 3,099,689 | 7/1963 | Cragg | 260/562 R |
| 4,094,905 | 6/1978 | Mizuno et al. | 260/561 R |

FOREIGN PATENT DOCUMENTS

| 863800 | 12/1952 | Fed. Rep. of Germany | 260/562 R |
| 31-6510 | 8/1956 | Japan . | |
| 718759 | 11/1954 | United Kingdom | 260/561 R |

OTHER PUBLICATIONS

Calderazzo, Inorg. Chem. 4 (1965), pp. 293-296.
Sternberg et al., J.A.C.S. 75 (1953), pp. 3148-3152.
Beckwith, TheChemistry of Amides, Interscience Publishers, N.Y., N.Y. 1970, p. 118.

*Primary Examiner*—Arthur P. Demers
*Attorney, Agent, or Firm*—Armstrong, Nikaido, Marmelstein & Kubovcik

[57] ABSTRACT

Dimethyl formamide is produced in high yield with good selectivity by reaction of monomethylamine and trimethylamine, or together with dimethylamine, with carbon monoxide in the presence of metallic iron or an iron compound such as oxide, hydroxide, sulfide, inorganic acid salt, organic acid salt or carbonyl compound of iron.

14 Claims, No Drawings

PROCESS FOR PRODUCING DIMETHYL FORMAMIDE

This invention relates to a process for producing dimethyl formamide by reaction of methylamines with carbon monoxide, and more particularly to the process characterized by using metallic iron or an iron compound as a catalyst.

Generally, dimethyl formamide is produced by reaction of dimethylamine with carbon monoxide or methyl formate, and such dimethylamine is usually prepared from methyl alcohol and ammonia by dehydration, but a large amount of monomethylamine and trimethylamine are inevitably by-produced besides dimethylamine in such dehydration. However, a commercial demand for monomethylamine and trimethylamine is smaller than that for dimethylamine, and thus most of these two amines are usually recycled to the methylamine synthesis system, where they are converted to dimethylamine. Thus, a direct synthesis of dimethyl formamide from the monomethylamine and trimethylamine having the smaller commercial demand will bring about a remarkable rationalization in the methylamine production industry, and thus will have a great commercial significance.

To meet such an expectation, U.S. Pat. No. 2,677,707 proposes a process comprising reacting monomethyl amine and/or dimethylamine, or further together with trimethylamine, with carbon monoxide in the presence of cuprous chloride, cupric chloride, potassium acetate, boron trifluoride or ammonium chloride as a catalyst. However, a selectivity of monomethylamine and trimethylamine to dimethyl formamide is low in said process and thus the process is not satisfactory as an industrial scale process.

U.S. Pat. No. 3,446,842 discloses a process for synthesizing dimethyl formamide from trimethylamine, ammonia and carbon monoxide in the presence of dicobalt octacarbonyl as a catalyst, but the process has such disadvantages as a long reaction time, etc., and thus is not always satisfactory as an industrial scale process.

As a result of extensive studies of the process for producing dimethyl formamide from monomethylamine and trimethylamine as starting materials, the present inventors have found a process for producing dimethyl formamide in high yield by reaction of monomethylamine and trimethylamine with carbon monoxide, using metallic iron or an iron compound as a catalyst.

The catalyst used in the present invention is metallic iron or an iron compound, and examples of the iron compound include oxides, hydroxides, sulfides, inorganic acid salts such as sulfates, carbonates, etc., organic acid salts, such as formates, oxalates, acetates, etc. of iron and carbonyl compounds of iron such as iron pentacarbonyl, etc.

It seems that the metallic iron and iron compounds other than carbonyl compounds perform a catalytic action after being converted to iron pentacarbonyl or further complicated iron carbonyl compounds under reaction conditions, but their state and forms have not been clarified yet. It seems that also the iron carbonyl compound is not always in the form as added, and may be converted to iron carbonyl compound of another form.

In the present invention, use of the so-called solvent is not essential, but addition of a small amount of a solvent assures the presence of a liquid phase portion even at an initial stage of reaction at a temperature above the critical temperature of amines as the stating material, and can facilitate a temperature control and increase the yield. Examples of such a solvent applicable to the present invention includes solvents of amide system such as dimethyl formamide, N-methylpyrolidone, etc., saturated aliphatic hydrocarbons such as hexane, heptane, octane, etc., and aromatic hydrocarbons such as benzene, toluene, xylene, etc.

In the present invention, the catalyst is used in an amount of 0.01-300 mg-atom, preferably 0.1-300 mg-atom in terms of iron atom on the basis of one mold of the amines as the starting material. If the catalyst is used in an amount less than said range, yield is lowered, whereas the amount of the catalyst over said range is applicable, but not economical.

A molar ratio of trimethylamine to monomethylamine used in the present invention is 0.3-10, preferably 0.5-5. Ratio outside said range is not practical, because an amount of unreacted material or yield of monomethyl formamide is increased. The yield of monomethyl formamide is increased at a lower molar ratio of said range, but according to the studies made by the present inventors monomethyl formamide reacts with trimethylamine and carbon monoxide under the reaction conditions of the present invention, whereby dimethyl formamide is formed. Thus, the monomethyl formamide can be recycled to the reaction system, where the recycled monomethyl formamide acts also as the solvent at the initial stage of reaction. In that case, a molar ratio of trimethylamine to the sum total of monomethyl formamide and monomethylamine must be adjusted to said range of the molar ratio of trimethylamine to monomethylamine.

In the present invention, reaction is carried out under a pressure of 10 kg/cm² gage or higher, preferably 50-500 kg/cm² gage. A pressure below said range is not preferable, because side reactions are accelerated, whereas a pressure higher than said range is not objectionable from the viewpoint of reaction, but too high a pressure is not practical from the viewpoint of economy.

Carbon monoxide plays not only a role of starting material, but also a role of maintaining reaction pressure. Thus, carbon monoxide is used in a great excess, but may be used in a mixture with an inert gas such as nitrogen, etc., so long as a partial pressure of carbon monoxide is 10 kg/cm² gage or higher.

The reaction is carried out at a temperature of 50°-350° C., preferably 100°-300° C. At a temperature below 50°C., a satisfactory reaction rate cannot be obtained, whereas at a temperature above 350°C., decomposition of product and decrease in yield are inevitable.

The reaction can be carried out batchwise or continuously.

The reaction in the present invention seems to proceed according to the following reaction equation, so far as the starting materials and the product are concerned:

$$CH_3NH_2 + (CH_3)_3N + 2CO \rightarrow 2HCON(CH_3)_2$$

It has not been clarified yet what reactions take place in the course from said starting materials to the product, but it is obvious that different reactions from the reaction to form dimethyl formamide from dimethylamine and carbon monoxide take place, and thus it is quite unexpectable whether the catalyst effective upon the reaction to form dimethyl formamide from dimethylamine and carbon monoxide is also effective or not upon the reactions of the present invention.

It is however well known from Japanese Pat. Publication No. 6510/56 that an iron carbonyl is effective upon the reaction to form dimethyl formamide from dimethylamine and carbon monoxide, and according to the studies made by the present inventors all catalysts of the present invention including the iron carbonyl are effective upon said reaction, and thus an inclusion of dimethylamine in the starting materials of the present invention is not objectionable. Therefore, it is possible to use a mixture of methylamines, for example, obtained by removing unreacted materials and by-products from a product mixture resulting from reaction to synthesize methylamines from methyl alcohol and ammonia, as such, as a starting material, without separating the mixture into individual amines. In that case, there is no specific restriction to the molar ratio of dimethylamine to other methylamines, but practically in view of using the mixture of methylamines from the methylamine synthesis reaction as a starting material, a molar ratio of dimethylamine to the sum total of monomethylamine and trimethylamine is 0.1-2.

As described above, dimethyl formamide can be produced in very high yield with a good selectivity in the present invention. Furthermore, dimethyl formamide can be produced from both monomethylamine and trimethylamine having a smaller demand among three methyl amines formed from methanol and ammonia, and thus the present process have a very remarkable commercial significance.

The present invention will be described in detail below, referring to Examples.

EXAMPLE 1

202.8 m moles of monomethylamine, 180.7 m moles of trimethylamine, 7.0 m moles of iron pentacarbonyl as a catalyst, and 6.0 g of N-methylpyrolidone as a solvent were charged into an autoclave having a net capacity of 100 ml, and subjected to reaction in the presence of carbon monoxide under a pressure of 250 kg/cm$^2$ gage of carbon monoxide and at a temperature of 237° C. for two hours. The resulting product was analyzed by gas chromatography, and it was found that 233.8 m moles of dimethyl formamide were produced.

EXAMPLE 2

Reaction was carried out in the same manner as in Example 1 except that no solvent (N-methylpyrolidone) was used. It was found that 221.1 m moles of dimethyl formamide were produced.

EXAMPLES 3-17

Reaction was carried out by changing molar ratio of starting materials, kind and amount of catalyst, pressure, temperature and reaction time, and the results are given in Table 1 together with the results of Examples 1 and 2.

EXAMPLE 18

A mixture of methylamines obtained by distilling a product containing 9.3% by weight of monomethylamine, 11.8% by weight of dimethylamine, 20.0% by weight of trimethylamine, 25.2% by weight of ammonia, 33.1% by weight of water and 0.6% by weight of others, resulting from reaction of methyl alcohol and ammonia at a molar ratio of $NH_3/CH_3OH$ of 1.30 in the presence of a silica-alumina catalyst (alumina: 13%) at a temperature of 452° C. under the atmospheric pressure and at a space velocity of 1,020 hr$^{-1}$, thereby removing ammonia, water, etc. therefrom, was used as a starting material.

Thus obtained mixture consisting of 139.7 m moles of monomethylamine, 123.1 m mole of dimethylamine and 124.2 m moles of trimethylamine, 7.0 m moles of iron pentacarbonyl as a catalyst, and 6.0 g of N-methylprolidone as a solvent were charged into an autoclave having a net capacity of 100 ml, and subjected to reaction in the presence of carbon monoxide under a pressure of 248 kg/cm$^2$ gage of carbon monoxide at a temperature of 240° C. for 2 hours.

The product was analyzed by gas chromatography, and it was found that 280.7 m moles of dimethyl formamide were produced.

EXAMPLES 19-21

Reaction was carried out by changing kind and amount of catalyst, molar ratio of starting materials, pressure, temperature and reaction time, and the results are shown together with the result of Example 18 in Table 2. The reactor was an autoclave having a net capacity of 100 ml.

TABLE 1

| Example No. | 1 | 2 | 3 | 4 | 5 | 6 | 7 | 8 | 9 |
|---|---|---|---|---|---|---|---|---|---|
| Catalyst | Fe(CO)$_5$ | Fe(CO)$_5$ | Fe$_2$O$_3$ | Fe | FeSO$_4$ . 7H$_2$O | Fe$_2$(SO$_4$)$_3$ . 9H$_2$O | FeS | Fe(OH)$_3$ | FeC$_2$O$_4$ . 2H$_2$O |
| Catalyst amount (in terms of iron) mg . atom | 7.0 | 7.0 | 6.2 | 6.4 | 6.4 | 6.4 | 6.4 | 6.4 | 6.4 |
| Catalyst ratio (in terms of iron) mg . atom/total amine mol | 18.3 | 18.3 | 16.2 | 16.6 | 16.1 | 16.5 | 16.2 | 16.7 | 16.6 |
| Monomethylamine m mol | 202.8 | 202.8 | 211.9 | 215.1 | 226.0 | 212.5 | 222.2 | 210.6 | 213.8 |
| Triethylamine m mol | 180.7 | 180.7 | 170.0 | 171.5 | 170.9 | 174.6 | 172.7 | 172.7 | 171.5 |
| Triethylamine/ monomethylamine (molar ratio) | 0.89 | 0.89 | 0.80 | 0.80 | 0.76 | 0.82 | 0.77 | 0.82 | 0.80 |
| Reaction pressure kg/cm$^2$ gage | 250 | 250 | 250 | 250 | 250 | 250 | 250 | 250 | 250 |
| Reaction temperature °C. | 237 | 237 | 240 | 238 | 238 | 240 | 240 | 236 | 239 |
| Reaction time hr | 2 | 2 | 4 | 6 | 2 | 4 | 6 | 6 | 2 |

TABLE 1-continued

| | | | | | | | | | |
|---|---|---|---|---|---|---|---|---|---|
| Monomethyl formamide yield m mol | 51.5 | 54.1 | 65.9 | 87.8 | 45.7 | 67.6 | 26.7 | 11.3 | 56.7 |
| Dimethyl formamide yield m mol | 233.8 | 221.1 | 214.2 | 165.1 | 316.0 | 240.8 | 225.2 | 290.6 | 224.0 |
| Dimethyl formamide yield based on total starting material amines % | 61.0 | 57.7 | 56.1 | 42.7 | 79.7 | 62.2 | 57.1 | 75.9 | 58.2 |
| Solvent (g) | N-methylpyrolidone 6.0 | none | N-methylpyrolidone 6.0 | N-methylpyrolidone 6.0 | N-methylpyrolidone 6.0 | N-methylpyrolidone 6.0 | N-methylpyrolidone 6.0 | N-methylpyrolidone 6.0 | N-methylpyrolidone 6.0 |

| Example No. | 10 | 11 | 12 | 13 | 14 | 15 | 16 | 17 |
|---|---|---|---|---|---|---|---|---|
| Catalyst | Fe(OH)(CH$_3$COO)$_2$ | Fe(CO)$_5$ | Fe(CO)$_5$ | Fe(CO)$_5$ | Fe(CO)$_5$ | Fe(CO)$_5$ | Fe(CO)$_5$ | Fe(CO)$_5$ |
| Catalyst amount (in terms of iron) mg . atom | 6.4 | 6.4 | 6.4 | 12.8 | 6.4 | 2.1 | 6.3 | 6.4 |
| Catalyst ratio (in terms of iron) mg . atom/total amine mol | 16.4 | 17.0 | 17.0 | 33.3 | 16.6 | 5.5 | 16.2 | 16.4 |
| Monomethylamine m mol | 215.4 | 204.4 | 204.4 | 213.1 | 213.1 | 202.8 | 97.5 | 250.0 |
| Triethylamine m mol | 175.6 | 173.0 | 173.0 | 171.4 | 171.4 | 180.7 | 292.5 | 140.0 |
| Triethylamine/monomethylamine (molar ratio) | 0.82 | 0.85 | 0.85 | 0.80 | 0.80 | 0.89 | 3.00 | 0.56 |
| Reaction pressure kg/cm$^2$ gage | 250 | 100 | 300 | 250 | 250 | 250 | 200 | 200 |
| Reaction temperature °C. | 240 | 235 | 237 | 150 | 280 | 238 | 238 | 239 |
| Reaction time hr | 2 | 4 | 4 | 6 | 2 | 6 | 4 | 4 |
| Monomethyl formamide yield m mol | 61.0 | 15.9 | 43.5 | 81.0 | 10.2 | 49.9 | 23.4 | 32.3 |
| Dimethyl formamide yield m mol | 248.2 | 243.9 | 278.0 | 205.5 | 303.9 | 174.4 | 124.7 | 288.6 |
| Dimethyl formamide yield based on total starting material amines % | 63.5 | 64.7 | 73.7 | 53.5 | 79.1 | 45.5 | 32.0 | 74.0 |
| Solvent (g) | N-methylpyrolidone 6.0 | N-methylpyrolidone 6.0 | N-methylpyrolidone 6.0 | N-methylpyrolidone 6.0 | N-methylpyrolidone 6.0 | N-methylpyrolidone 6.0 | N-methylpyrolidone 6.0 | N-methylpyrolidone 6.0 |

Table 2

| Example No. | 18 | 19 | 20 | 21 |
|---|---|---|---|---|
| Catalyst | Fe(CO)$_5$ | Fe(CO)$_5$ | Fe$_2$O$_3$ | Fe |
| Catalyst amount (in terms of iron) mg . atom | 7.0 | 7.0 | 6.2 | 6.2 |
| Catalyst ratio (in terms of iron) mg . atom/total amine | 18.1 | 18.5 | 16.2 | 16.5 |
| Monomethylamine m mol | 139.7 | 165.4 | 141.9 | 135.7 |
| Dimethylamine m mol | 123.1 | 62.4 | 126.1 | 120.0 |
| Trimethylamine m mol | 124.2 | 150.1 | 113.9 | 120.7 |
| Trimethylamine/monomethylamine (molar ratio) | 0.89 | 0.91 | 0.80 | 0.89 |
| Dimethylamine/mono + trimethylamines (molar ratio) | 0.47 | 0.20 | 0.49 | 0.47 |
| Reaction pressure kg/cm$^2$ gage | 248 | 248 | 250 | 247 |
| Reaction temperature °C. | 240 | 237 | 237 | 239 |
| Reaction time hr | 2 | 2 | 4 | 6 |
| Dimethyl formamide yield m mol | 280.7 | 257.3 | 246.3 | 166.4 |
| Dimethyl formamide yield based on total starting material amines % | 72.5 | 68.1 | 64.5 | 44.2 |
| Solvent (g) | N-methylpyrolidone 6.0 | N-methylpyrolidone 6.0 | N-methylpyrolidone 6.0 | N-methylpyrolidone 6.0 |

What is claimed is:

1. The process for producing dimethyl formamide which comprises reacting a mixture of methyl amines including as essential components monomethylamine and trimethylamine with carbon monoxide in the presence of an iron carbonyl at concentration of 5.5–300 mg- atom of iron per mole of reactant amine.

2. A process according to claim 1, wherein a molar ratio of trimethylamine to monomethylamine is 0.3–10.

3. A process according to claim 2, wherein the molar ratio of trimethylamine to monomethylamine is 0.5–5.

4. A process according to claim 1, wherein a molar ratio of trimethylamine to monomethylamine is 0.3–10 and a molar ratio of dimethylamine to sum total of monomethylamine and trimethylamine is 0.1–2.

5. A process according to claim 4, wherein the molar ratio of trimethylamine to monomethylamine is 0.5–5.

6. A process according to claim 4, wherein the reaction is carried out under a pressure of 10 kg/cm$^2$ gage or higher.

7. A process according to claim 6, wherein the reaction is carried out under a pressure of 50-500 kg/cm$^2$ gage.

8. A process according to claim 1, wherein the reaction is carried out in the presence of an inert gas when a partial pressure of carbon monoxide is at least 10 kg/cm$^2$ gage.

9. A process according to claim 1, wherein the reaction is carried out at a temperature of 50°-350° C.

10. A process according to claim 9, wherein the reaction is carried out at a temperature of 100°-300° C.

11. A process according to claim 1, wherein the reaction is carried out in the presence of a solvent.

12. A process according to claim 11, wherein the solvent is dimethyl formamide, N-methylpyrolidone, hexane, heptane, octane, benzene, toluene or xylene.

13. The process according to claim 1 wherein said iron carbonyl is formed as a result of adding a material capable of being converted to the iron carbonyl within said process.

14. The process according to claim 13, wherein said material capable of being converted to said iron carbonyl is selected from the group consisting of metallic iron and an oxide, hydroxide, sulfide, inorganic acid salt and organic acid salt of iron.

* * * * *